United States Patent [19]

Auweiler

[11] Patent Number: 5,785,677
[45] Date of Patent: *Jul. 28, 1998

[54] LAPAROSCOPY BAG

[76] Inventor: Udo Auweiler, Max-Baermann-Str. 19, 5060 Bergisch-Gladbach 1, Germany

[*] Notice: This patent issued on a continued prosecution application filed under 37 CFR 1.53(d), and is subject to the twenty year patent term provisions of 35 U.S.C. 154(a)(2).

[21] Appl. No.: 561,305

[22] Filed: Nov. 21, 1995

Related U.S. Application Data

[62] Division of Ser. No. 81,417, Jun. 22, 1993, abandoned.

[51] Int. Cl.⁶ ............... A61M 1/00; A61F 13/00
[52] U.S. Cl. ............... 604/28; 604/328; 600/37; 128/850; 128/DIG. 24
[58] Field of Search ............... 604/156, 322, 604/327, 328, 36, 37, 28, 27; 128/849, 850, DIG. 24, 897; 600/37; 383/36, 72, 75, 76, 907; 119/95

[56] References Cited

U.S. PATENT DOCUMENTS

| | | |
|---|---|---|
| 4,991,593 | 2/1991 | Le Vahn .................... 128/856 |
| 5,037,379 | 8/1991 | Clayman et al. .............. 604/27 X |
| 5,074,867 | 12/1991 | Wilk ......................... 604/264 X |
| 5,143,082 | 9/1992 | Kindberg et al. ............. 600/37 X |
| 5,147,371 | 9/1992 | Washington et al. ........... 606/127 |
| 5,190,555 | 3/1993 | Wetter et al. ................ 606/114 |
| 5,201,740 | 4/1993 | Nakao et al. ................. 606/113 |
| 5,215,521 | 6/1993 | Cochran et al. .............. 600/37 X |
| 5,224,930 | 7/1993 | Spaeth et al. ............... 606/167 X |
| 5,234,439 | 8/1993 | Wilk et al. .................. 606/114 |
| 5,352,184 | 10/1994 | Goldberg et al. ............. 600/37 |
| 5,486,182 | 1/1996 | Nakao et al. ................. 600/37 X |
| 5,647,372 | 7/1997 | Tovey et al. ................. 600/37 X |

*Primary Examiner*—Mary Beth Jones
*Attorney, Agent, or Firm*—Evenson, McKeown, Edwards & Lenahan, P.L.L.C.

[57] ABSTRACT

A laparoscopy bag of a flexible material with traction strings of drawstrings is provided at its opening or mouth, in particular for use in a trocar, and in which the bag consists of a working section to which a hose-shaped part or extension is attached or which is provided with a hose-shaped extension.

1 Claim, 3 Drawing Sheets

LAPAROSCOPY BAG

This is a divisional of application Ser. No. 08/081,417 filed on 22 Jun. 1993, now abandoned.

FIELD OF THE INVENTION

My present invention relates to a laparoscopy assembly including a laparoscopy bag adapted to receive resected tissue.

BACKGROUND OF THE INVENTION

It is well known for endoscopic operations (laparoscopy) the abdominal cavity is not opened by an abdominal incision, but that the instruments required as well as the optical system are introduced through a trocar pushed through the abdominal wall, the instruments being actuated from outside the abdominal cavity. To the patient this surgical method is less traumatizing than operations carried out so far which involved the opening of the abdominal cavity. This procedure results in less discomfort to the patient. He has less pain, the wound heals more rapidly and, correspondingly, the duration of hospitalization is reduced. This surgical practice, however, meets its limits as soon as large size tumors or large masses of tissue have to be removed from the abdominal cavity. If such material cannot be removed in bulk through the trocar the tumor and the inflamed tissue must be dissected within the abdominal cavity and may give rise to a contamination of the latter and constitute, in particular in the case of malignant tumors, a danger to the patient because of the possibility or metastases.

In order to solve this set of problems so-called "laparoscopy bags" have become known which are made of a flexible and durable material and which can be closed by pulling strings at their upper open end. This bag, hanging from the strings, is introduced into the abdominal cavity through the trocar and is opened in the abdominal cavity where the tissue to be removed is placed in the bag. After that the bag is closed by pulling the strings and its upper openable end is withdrawn from the abdominal wall together with the trocar. Thereafter the tissue is dissected and the individual lumps are taken out of the small bag, whereupon the bag is discarded. Although this laparoscopy bag constitutes a considerable improvement since—at least theoretically—no impurity can get into the abdominal cavity, the withdrawal of the resected and dissected tissue is complicated and time-consuming. In addition, the danger still exists that during the withdrawal of the dissected tissue, particles may be introduced into a vessel and, in the case of malign tumors, may give rise to metastases.

Beyond that, hose-shaped laparoscopy bags have been known which are filled with the resected and dissected lumps of tissue and which are withdrawn through a trocar. These bas are provided with a lap enabling the bag to be withdrawn. These bags, however, have the essential shortcoming that no working space is provided where the surgical operation can be carried out and where the lumps of tissue can safely be dissected. Therefore a contamination of the abdominal cavity cannot be excluded.

OBJECT OF THE INVENTION

The object of the present invention is to provide a laparoscopy bag allowing the in-toto withdrawal in the closed bag of the resected and dissected tissue through the trocar, i.e. the withdrawal of the closed bag filled with tissue, sot hat the danger of tissue particles penetrating into the vessels of the organism is excluded.

SUMMARY OF THE INVENTION

This object is achieved, in accordance with the invention, with a laparoscopy bag of a flexible material with traction strings or drawstrings provided on its opening or mouth, in particular for use in a trocar and in which the bag consists of a working section to which a hose-shaped part or extension is attached or which is provided with a hose-shaped extension.

The laparoscopy bag consists of a working section sufficient in size to accommodate the material to be resected. The tissue dissected therein drops into the hose-shaped part or is forced into this hose-shaped reservoir when the bag has been closed and is pulled into the trocar, so that the bag may be withdrawn as a whole. The hose-shaped part serving as the reservoir has a diameter slightly smaller than that of the trocar. The hose-shaped part can be conceived as a straight hose or as a folded bellows.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
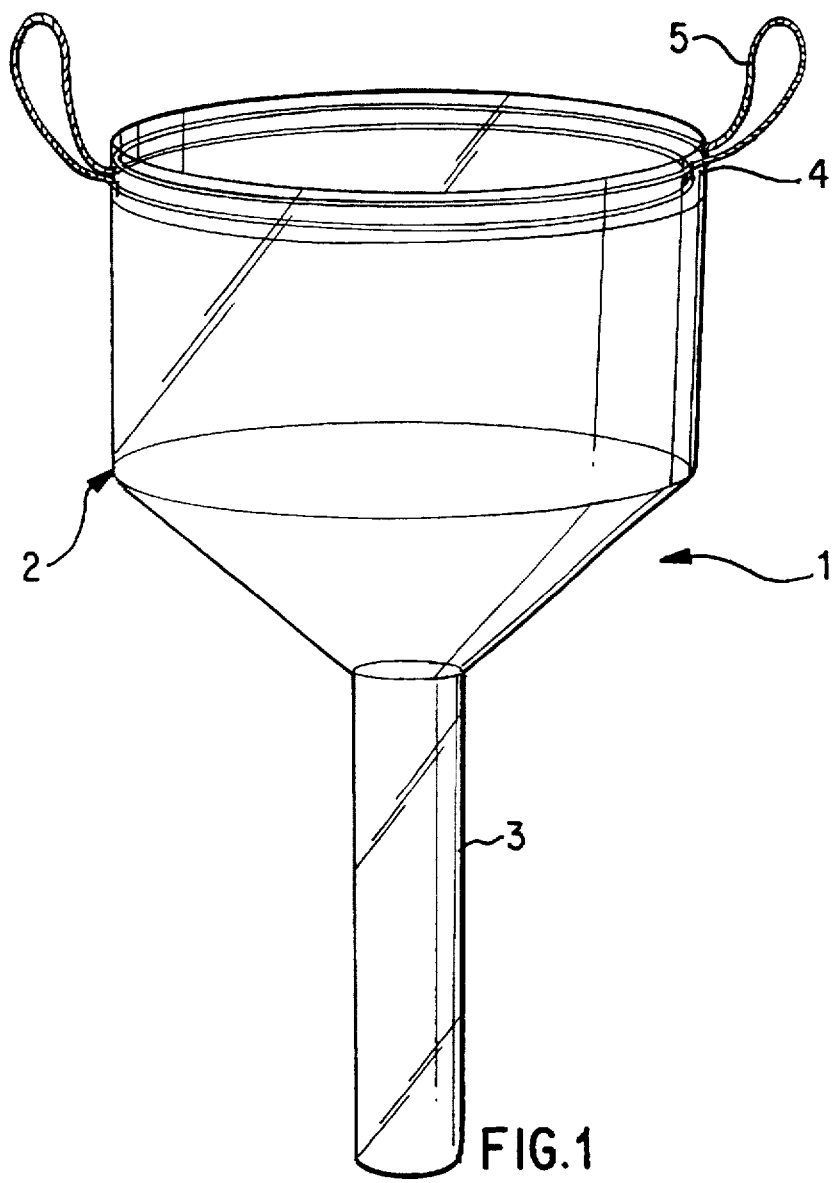
FIG. 1 is a schematic drawing of the laparoscopy bag.

FIG. 1 schematically shows a laparoscopy bag 1 according to the invention. The bag is subdivided into the working section 2 and the hose-shaped reservoir 3. The working section 2 has a circular cross section and and, like a funnel, is tapered off to the hose-shaped reservoir. The upper rim 4 of bag 1 is provided with traction strings 5 for closing the bag. The diameter of reservoir 3 is slightly smaller than that of the trocar used for the surgical operation. In FIG. 1 a straight hose is used as the reservoir. The laparoscopy bag 1 is made of a clear transparent foil with a certain strength enabling the bag to be opened in the abdominal cavity and to retain the opened position. The material of the bag shall be antistatic, pyrogen-free, non-toxic and sterilisable.

The working space of the working section 2 usually has a diameter of 15 cm but, depending on the volume of tissue to be resected, bags having other dimensions can be imagined.

Figure 2:
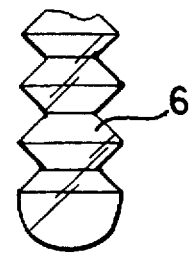
FIG. 2 is an elevation of one design of the hose-shaped part.

FIG. 2 shows a modification of the reservoir, i.e. a folded bellows 6, allowing the available reservoir volume to be increased it required.

Figure 3:
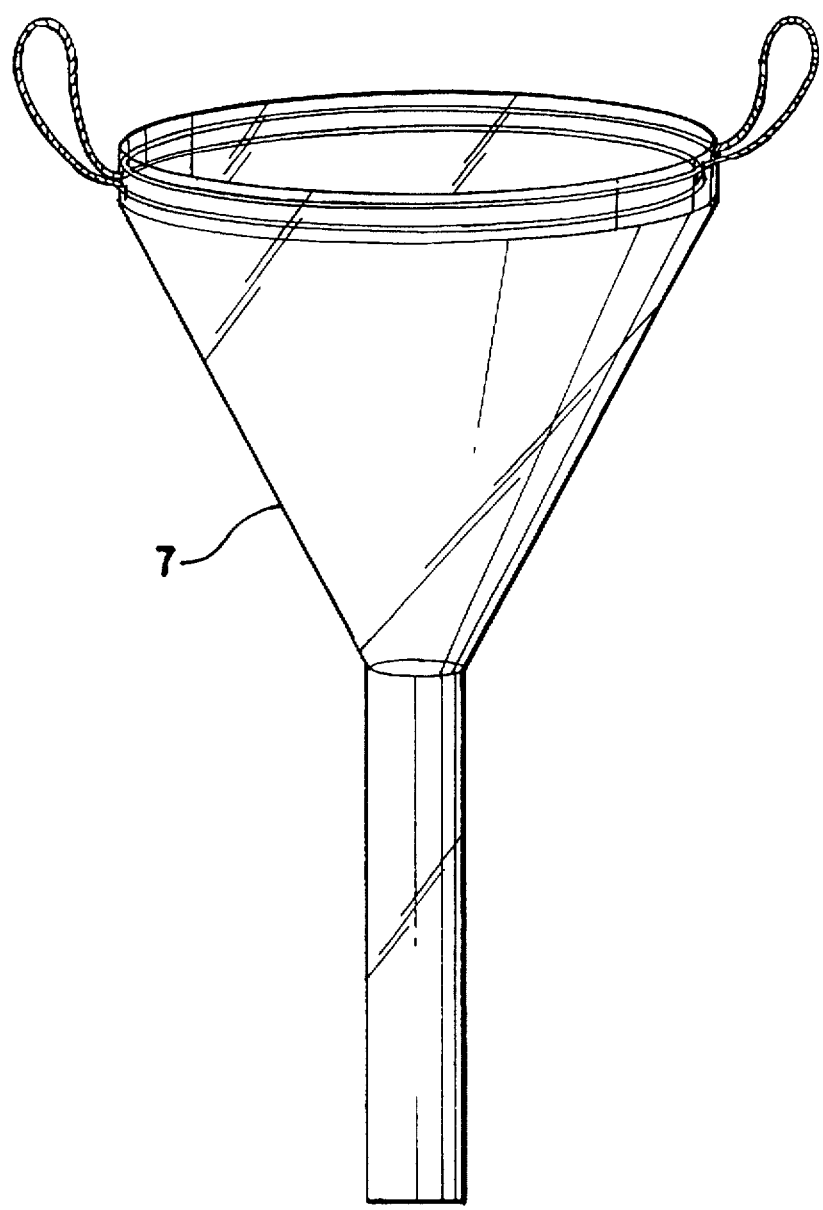
FIG. 3 is a diagram of another laparoscopy bag.

FIG. 3 shows a laparoscopy bag the working section of which is funnel-shaped, but which in the other aspects is identical with the design according to FIG. 1. This modification is suitable for smaller lumps of tissue and for tissue having a soft consistency which can easily be dissected.

Prior to use the laparoscopy bag according to the invention is either rolled up from the side of the reservoir to form a coil which can simply be introduced into the abdominal cavity through the trocar. Another possibility consists in accommodating the working section in the hose-shaped reservoir 3, with the traction strings freely projecting over the reservoir. In the abdominal cavity the bag can then easily be unfolded with the aid of two instruments.

Figure 4:
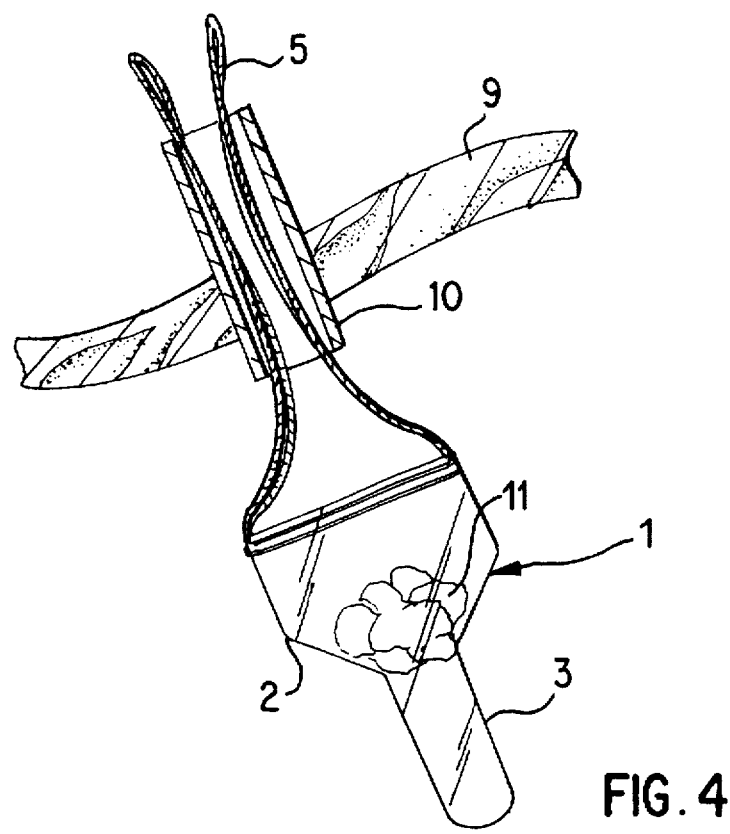
FIG. 4 is a diagram which illustrates the positions of the trocar and the bag in the abdominal cavity.
Figure 5:
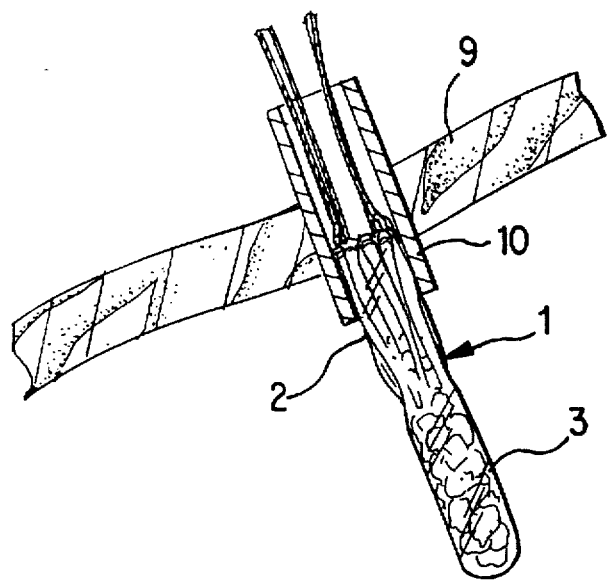
FIG. 5 is a diagram which illustrates the withdrawal of the bag after the tissue to be removed has been deposited in the bag and dissected.

The application of the laparoscopy bag is explained with the aid of FIGS. 4 and 5. After the the diagnostic laparoscopy a trocar, by preference of 2 cm, is applied through the abdominal wall 9. The sterile, folded bag is then introduced through this trocar into the abdominal cavity and is opened there using two blunt instruments. This phase is represented in FIG. 4, the two traction strings being represented as projecting over the trocar. Of course, it is also possible to introduce the traction strings together with the bag into the abdominal cavity and then to actuate the traction strings by appropriate instruments. After that the tumor or the tissue to be removed are resected and placed in the working section of the bag. The tumor can then be dissected in the bag by scissors or surgical knives, whereby care should be taken not to damage the bag and not to allow resected tissue to penetrate into the abdominal cavity. As soon as the tissue 11 has been dissected to such a degree that it can be accommodated in the reservoir 3 the bag is closed with the aid of the two traction strings. After that the bag is drawn through the trocar by pulling the traction strings. As soon as the bag has reached the trocar it is squeezed, so that—because of the shape of the bag according to the invention—the dissected tissue, as far as it has not yet slipped into the reservoir, is forced from the working section of the bag into the reservoir. This position is shown in FIG. 5. After that the complete bag, together with the tissue in the reservoir, can be withdrawn from the trocar without any problem. In this way it is made sure that no tissue particles penetrate into the abdominal cavity and that any contamination of the abdominal cavity is prevented.

I claim:

1. A method of excising tissue from an abdominal cavity, comprising the steps of:

(a) inserting through an abdominal wall a trocar having an internal diameter and communicating with an abdominal cavity;
(b) introducing into said abdominal cavity in a collapsed state a laparoscopy bag, said laparoscopy bag being composed of flexible material and consisting essentially of:
 a relatively large diameter working section having a circular cross section and an open mouth and adapted to receive resected tissue and instruments for dissecting resected tissue in said working section,
 a hose-shaped extension closed at a free end and connected with said working section centrally opposite said mouth and extending away from said working section, said hose-shaped extension being of a smaller diameter than said mouth and so dimensioned that said hose-shaped extension, when filled with resected tissue, can be withdrawn from said cavity through said trocar,
 a tapered, funnel-shaped portion connecting said working section with said extension, and
 drawstrings at said mouth for closing same prior to withdrawal of said bag through said trocar;
(c) opening said bag within said cavity;
(d) resecting tissue within said abdominal cavity;
(e) introducing resected tissue into said bag through said mouth in said cavity;
(f) drawing said mouth closed with said drawstrings;
(g) drawing the bag against the trocar to squeeze the bag and force resected tissue from the working section of the bag into the hose-shaped extension; and
(h) pulling said bag with said hose-shaped extension filled with resected tissue out of said cavity through said trocar with said drawstrings.

\* \* \* \* \*